Figure 1:
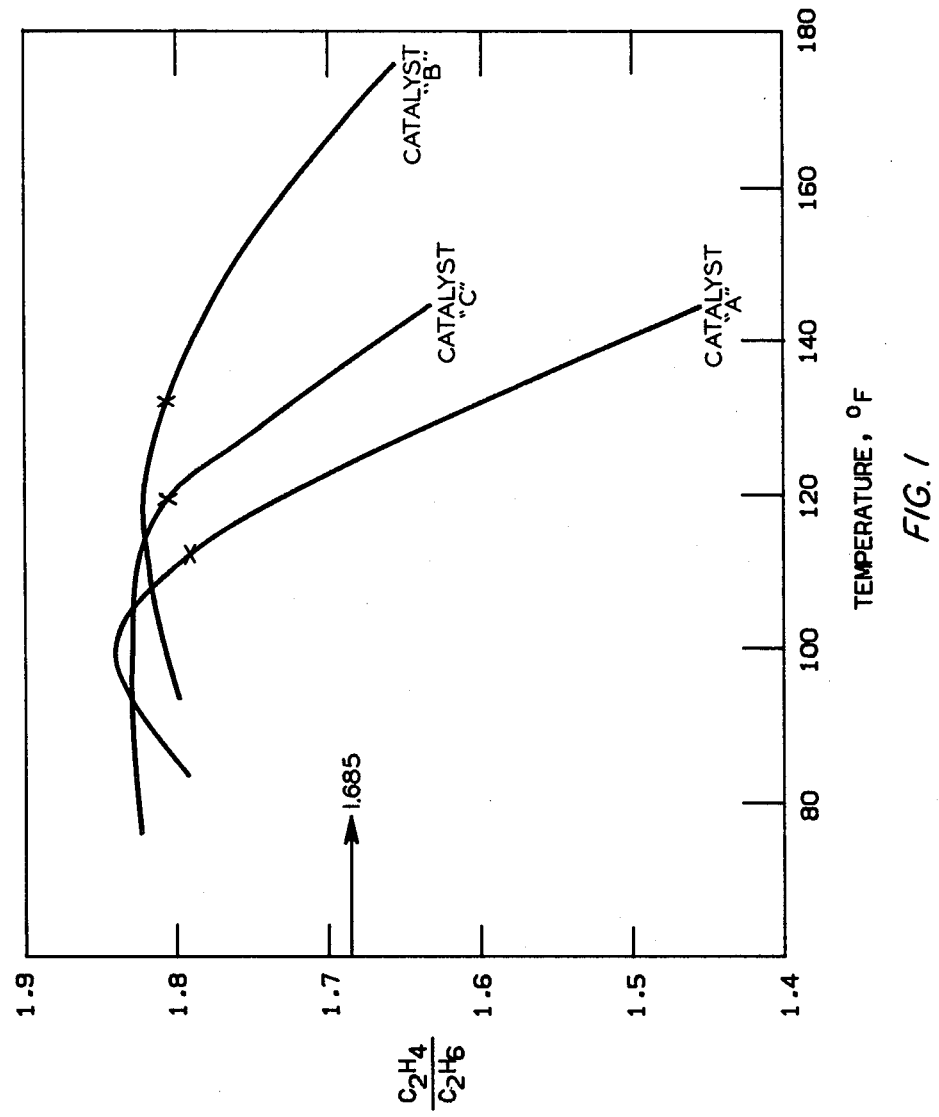

United States Patent [19]

Johnson et al.

[11] Patent Number: 4,484,015
[45] Date of Patent: Nov. 20, 1984

[54] SELECTIVE HYDROGENATION

[75] Inventors: Marvin M. Johnson; Darrell W. Walker; Gerhard P. Nowack, all of Bartlesville, Okla.

[73] Assignee: Phillips Petroleum Company, Bartlesville, Okla.

[21] Appl. No.: 506,951

[22] Filed: Jun. 22, 1983

Related U.S. Application Data

[62] Division of Ser. No. 260,946, May 6, 1981, Pat. No. 4,404,124.

[51] Int. Cl.$^3$ .............................................. C07C 5/08
[52] U.S. Cl. .................................... 585/262; 585/259
[58] Field of Search ..................... 585/259, 262, 260

[56] References Cited

U.S. PATENT DOCUMENTS

| 2,802,889 | 8/1957 | Frevel et al. | 585/262 |
| 4,404,124 | 9/1983 | Johnson et al. | 585/259 |
| 4,409,410 | 10/1983 | Cosyns et al. | 585/259 |

Primary Examiner—Delbert E. Gantz
Assistant Examiner—Anthony McFarlane
Attorney, Agent, or Firm—Edward L. Bowman

[57] ABSTRACT

A catalyst and process for the selective hydrogenation of acetylene, said catalyst comprising palladium and silver with the palladium concentrated as a skin and the silver distributed throughout.

10 Claims, 1 Drawing Figure

SELECTIVE HYDROGENATION

This is a divisional of application Ser. No. 260,946, filed May 6, 1981, now U.S. Pat. No. 4,404,124.

This invention relates to a new catalyst for the selective hydrogenation of acetylene as well as a method for making such catalyst and to a method for the selective hydrogenation of acetylene in admixture with ethylene.

Ethylene is a monomer that is used in preparing a number of olefin polymers. Ethylene is generally made by the pyrolysis or catalytic cracking of refinery gas, ethane, propane, butane, and the like. Ethylene so produced usually contains small proportions of acetylene. In polymer grade ethylene, it is generally preferred that the acetylene content be less than about 10 ppm, most preferably less than about 5 ppm.

One of the techniques that has been used in the past for reducing the amount of acetylene in an ethylene stream has involved selective hydrogenation using a catalyst comprising palladium supported on an activated alumina carrier. Numerous factors have been found to affect the selectivity of such palladium catalysts.

Typically, as the temperature is increased above that which gives substantial elimination of acetylene, there is a progressive increase in the amount of ethylene and acetylene that is converted to ethane. As the amount of olefin that is hydrogenated increases typically, the temperature of the catalyst also increases resulting in runaway ethylene hydrogenation. Since ethylene is the desired product and since some temperature fluctuations are to be expected in commercial scale operations, it is obviously desirable to be able to operate with catalyst and conditions that will allow a relatively wide spread between the temperature which produces the substantial elimination of acetylene and the temperature that cause levels of ethane production that are intolerable. Generally, it is desirable to use a catalyst with which there is at least about a 30° F. temperature difference between substantially complete acetylene removal and incipient runaway.

It has recently been discovered that a particularly active catalyst for selective acetylene hydrogenation results when the palladium is concentrated near the surface of the alpha alumina particles. Such "skin" catalysts are less sensitive to the effects of the carbon monoxide concentration in the feed than catalysts in which the palladium is more widely distributed in the catalyst particles. However, when such "skin" catalysts are employed on feedstreams containing less than about 600 ppm carbon monoxide, it has been noted that the temperature range between substantially complete acetylene removal and runaway ethylene hydrogenation is not as broad as would be desired. This temperature range decreases as the carbon monoxide content of the feedstream is reduced. When such "skin" catalysts are employed on hydrocarbon streams containing levels of CO lower than about 600 ppm runaway olefin hydrogenation can even occur before there has been substantially complete acetylene hydrogenation.

It is well recognized that the amount of carbon monoxide in the effluent from an ethane cracker can vary over a large range depending on the operating conditions, the character of the feed to the cracker, and the like. Accordingly, it is desirable to find a way to make the "skin" type palladium catalysts less sensitive to variations in the carbon monoxide content of the ethylene-containing feedstream.

An object of this invention is to provide a method, and catalysts, for the treatment of gas mixtures comprising ethylene and acetylene whereby the acetylene is selectively and substantially consumed.

A further object is to provide such a method and catalysts whereby acetylene in admixture with ethylene is hydrogenated to form a further amount of ethylene, without the concurrent consumption of a significant proportion of ethylene.

Another object is to provide such a method and catalysts whereby the operations can be continued for a prolonged time on a large scale without occurrence of a dishabilitating proportion of side reactions such as carbonization and polymerization.

Still another object of the present invention is to reduce the extent to which palladium "skin" type catalysts are affected by the carbon monoxide content of the hydrogenation feed.

FIG. 1 is a graph illustrating the advantages of the present invention.

The novel hydrogenation catalyst of the present invention comprises particles of alpha alumina containing palladium and silver. The palladium is about 0.01 to about 0.025 weight percent of the catalyst. The weight percent silver is at least twice that of the palladium. The inventive catalyst is further characterized in that at least 90 weight percent of the particles of alpha alumina have the palladium concentrated in an area within 300 microns of the exterior surface while the silver is distributed throughout the particles. For reasons of economics, the amount of silver in the catalyst is generally not more than about 10 times that of the palladium, preferably it is in the range of about 2 to about 6 times that of the palladium.

Any suitable alumina can be employed which will result in a catalyst having an alpha alumina support. Typical alpha aluminas have surface areas in the range of about 3 to about 7 square meters per gram, pore volume of about 0.24 to about 0.34 cubic centimeters per gram, and a mean pore radius in the range of about 685 to about 2270 Angstrom units.

These characteristics of the alpha alumina can be determined using the following methods on samples of the alumina that has been degassed at room temperature for 30 minutes at a pressure of $10^{-3}$ mm or less:

(1) The surface area is found by the well-known method of Brunauer, Emmett, and Teller by measuring the quantity of argon adsorbed on the catalyst at $-183°$ C. with the cross-sectional area of the argon atom being taken as 14.4 square Angstrom units.

(2) Determining the pore volume involves determining the "mercury density" and the "helium density". The mercury density is determined by immersing the support in mercury at 20° C. and 900 mm pressure, under which conditions about 15 minutes are allowed for attainment of equilibrium. The helium density is determined by immersing the support in helium at room temperature. The pore volume per gram is found by subtracting the reciprocal of the "helium density" from the reciprocal of the "mercury density".

(3) The mean pore radius is determined by the formula $$\bar{r} = 2V/A$$

where $\bar{r}$ is the mean pore radius, $V$ is the pore volume, and $A$ is the surface area. If $V$ is expressed in cubic centimeters and A is expressed in square centimeters, the mean radius $\bar{r}$ is in centimeters and should be multiplied by $10^8$ to give the mean radius in Angstrom units.

The palladium can be placed on the alumina in any suitable manner that will yield a catalyst meeting the above-described parameters. The presently preferred technique involves impregnating the alumina with an aqueous solution of palladium chloride. The extent of penetration of the palladium can be controlled by adjustment of the acidity of the solution with hydrochloric acid.

The catalyst particles can be of any suitable shape and dimensions, however, the advantages of the skin type catalyst are particularly notable for those particles having minimum dimensions of at least about 1 millimeter. A particularly suitable form of catalyst particle is one having dimensions in the range of about 2 to about 6 millimeters.

One can use any suitable method to determine whether at least 90 weight percent of the catalyst particles have the palladium concentrated in an area within 300 microns of the exterior surface. One technique currently favored involves breaking open a representative sample of catalyst pills and treating them with a dilute alcoholic solution of N,N-dimethyl-para-nitrosoaniline. The treating solution reacts with the palladium to give a red color which can be used to evaluate the distribution of the palladium.

The silver can be distributed throughout the catalyst in any suitable manner. It is currently preferred to employ an aqueous silver nitrate solution is a quantity greater than that necessary to fill the pore volume of the catalyst. Attempts to improve the sensitivity of the catalyst by using incipient impregnation have not been successful, even when solutions were used that should have provided a 5 to 1 weight ratio of silver to palladium. This is considered to result from imperfect contacting which leaves significant amounts of catalyst particles with deficient amounts of silver.

The impregnated catalyst is dried at a temperature in the range of about 25° C. to about 150° C.

The dried catalyst can be employed directly as a catalyst for hydrogenation, however, preferably it is roasted to decompose the compounds providing the palladium and silver. This roasting can be done at temperatures up to about 500° C., temperatures in the range of 150° C. to 450° C. being preferred. The roasting is also preferably followed by a reduction step. This reduction can be accomplished using the feed for the selective hydrogenation; however, it is preferable to reduce the catalyst with a gas such as hydrogen since optimum operation of the selective hydrogenation does not begin until there has been reduction of the catalytic metals. Typically, the reduction is carried out at a temperature in the range of about 25° C. to about 450° C.

The selective hydrogenation is carried out by passing the gas stream of ethylene, containing the acetylene to be removed, along with hydrogen into contact with the catalysts of the present invention. In order to best approach substantially complete removal of the acetylene, there should be at least one mole of hydrogen for each mole of acetylene.

The temperature necessary for the selectivity hydrogenation depends largely upon the activity of the catalyst and the extent of acetylene removal desired. Generally temperatures in the range of about 35° C. to about 100° C. are used. Any suitable reaction pressure can be employed. Generally, the total pressure is in the range of about 100 to about 1,000 pounds per square inch gauge. The gas hourly space velocity (GHSV) can also vary over a wide range. Typically, the space velocity will be in the range of about 1,000 to about 10,000 liters of feed per liter of catalyst per hour, more preferably about 2,000 to about 8,000.

Regeneration of the catalyst may be accomplished by heating the catalyst in air at a temperature preferably not in excess of 500° C. to burn off any organic matter, polymer, or char.

The high loading of silver relative to the palladium in the present catalysts is also expected to make the catalysts less sensitive to being poisoned by arsenic that may be present in the feed.

A further understanding of the present invention and its advantages will be provided by the following examples.

EXAMPLE I

Catalyst Preparations

First, a skin-type catalyst was prepared by impregnating alpha alumina pills (3/16"×3/16") with an aqueous solution of palladium acidified with hydrochloric acid to produce a catalyst containing about 0.017 weight percent palladium. Over 90 percent of the resulting catalyst pills had the palladiium deposited in the peripheral 300 micrometers. This catalyst will be designated as Catalyst A.

Another catalyst was prepared by immersing at room temperature 36.3 grams of Catalyst A in 20 milliliters of water having 0.057 grams of silver nitrate dissolved therein. The catalysts pills were stirred around in the solution for a few minutes, then the excess solution was decanted. Ten millimeters of the solution was recovered. The recovered solution was analyzed and the silver nitrate content was 0.015 molar whereas that of the starting solution was 0.0168. The catalyst was dried by evaporation and then calcined in air for one hour at about 370° C. The silver content, as calculated from the amount of silver nitrate taken up by the catalyst, was about 0.055 weight percent of the catalyst. This catalyst will be referred to as Catalyst B.

Still another catalyst was prepared by immersing at room temperature 47.2 grams of Catalyst A in 25 milliliters of water containing 0.0372 grams of silver nitrate. The catalysts pills were swirled for about 3 minutes and then the excess liquid decanted. The catalyst was dried and calcined as was done in preparing Catalyst B. This catalyst is denoted herein as Catalyst B. By assuming that the catalyst retained the same fraction of silver from the silver nitrate solution as Catalyst A did, Catalyst C can be calculated to contain about 0.028 weight percent silver.

EXAMPLE II

Comparative Hydrogenation Reactions

Runs were made using the catalysts of Example I to determine their selectivity to hydrogenate acetylene to ethylene. 20 mL portions of catalysts were placed in an 0.5 inch I.D. stainless steel reactor mounted vertically in an electrically-heated temperature-controlled tube furnace. The space above and below the catalysts was filled with glass beads. A 3/16" coaxial thermowell in the reactor contained a traveling thermocouple to measure catalyst temperature. Feedstock from an ethane cracking furnace passed downflow through the reactor.

The composition of the feedstock for these runs is shown in Table I.

TABLE I

| Compound | Conc., Mole % |
|---|---|
| $H_2$ | 24.1 |
| CO | 0.025 |
| $CH_4$ | 11.5 |
| $C_2H_2$ | 0.27 |
| $C_2H_4$ | 40.5 |
| $C_2H_6$ | 22.9 |
| $C_3H_6$ | 0.70 |
| $C_3H_8$ | 0.02 |

The procedure followed in making runs was to purge and pressurize the reactor to 200 psig, the pressure used in all runs. After the desired temperature had been obtained, feedstock was introduced at about 2,600 GHSV. Reactor effluent passed through 300 mL glass sample bombs and, when desired, bombs were closed and removed for GC Analysis using two ⅛"×6' columns in series that contained Chromosorb 102 and Poropak T.

A nunber of successive runs were made with each catalyst using incrementally higher temperatures. Plots were made of the ratio of ethylene to ethane in the reactor effluent samples taken at the various reaction temperatures. The results are shown in FIG. 1. The curves show that the increase in ethane production with increased temperature is much less dramatic for Catalysts B and C than for control Catalyst A.

Another way of illustrating the superiority of Catalysts B and C is to compare the temperature spread between that which provides substantial elimination of acetylene and that which provides an arbitrarily selected level of ethane. The "X" marks on the respective curves notes the temperature at which acetylene was no longer detected (i.e. less than 5 ppm). The value of 1.685 for a molar ratio of ethane to ethylene was selected since that is a value in the area where runaway is exhibited with Catalyst A. This comparison is shown in Table II wherein $\Delta T$ is the difference between the temperature at which the acetylene could no longer be detected and the temperature at which the ethylene to ethane ratio decreased to 1.685.

TABLE II

| Catalyst | Ag, Wt. % | $\Delta T$, °F. |
|---|---|---|
| A | 0 | 12 |
| B | 0.055 | 38 |
| C | 0.028 | 18 |

These results show that when the weight ratio of silver to palladium is less than 2 to 1 there is little improvement in $\Delta T$. The results obtained with Catalyst B, however, shows that larger levels of silver do provide a significant improvement in the $\Delta T$.

What is claimed is:

1. A method for the treatment of a gaseous mixture comprising ethylene and acetylene, which method comprises selectively hydrogenating the acetylene therein by contacting said mixture together with hydrogen with a catalyst consisting essentially of particles of alpha alumina containing metallic components consisting essentially of palladium and silver wherein the palladium is about 0.01 to about 0.025 weight percent of the catalyst, the weight percent silver is at least twice that of the palladium, the silver is distributed throughout said catalyst particles, and substantially all of the palladium is concentrated in an area within 300 microns of the exterior surface of at least 90 percent of the catalyst particles.

2. A method according to claim 1 wherein said gaseous mixture contains less than about 600 ppm of carbon monoxide.

3. A process according to claim 2 wherein the weight ratio of silver to palladium in said catalyst is no greater than about 10.

4. A method according to claim 3 wherein the dimensions of the catalyst particles are in the range of about 2 to about 6 milliliters.

5. A method according to claim 4 wherein the weight ratio of silver to palladium is in the range of about 2 to about 6.

6. A method according to claim 5 wherein said alpha alumina has surface area in the range of about 3 to about 7 square meters per gram, pore volume of about 0.24 to about 0.34 cubic centimeters per gram, and a mean pore radius in the ranges of about 685 to about 2,270 Angstrom units.

7. A method according to claim 6 wherein the hydrogenation temperature is in the range of about 35° C. to about 100° C. and the space velocity is in the range of about 2,000 to 8,000.

8. A method according to claim 7 wherein said gaseous mixture contains no more than about 250 ppm of carbon monoxide.

9. A method according to claim 8 wherein said catalyst is prepared by impregnating alumina particles with a solution of palladium chloride acidified with hydrochloric acid, then mixing the particles with an amount of an aqueous solution of silver nitrate in excess of the pore volume of the alumina.

10. A process according to claim 9 wherein said catalyst contains about 0.02 weight percent palladium.

* * * * *